United States Patent [19]
Wallshein

[11] 4,224,022
[45] Sep. 23, 1980

[54] ORTHODONTIC FACE BOW

[76] Inventor: Melvin Wallshein, 8645 Bay Pkwy., Brooklyn, N.Y. 11214

[21] Appl. No.: 946,875

[22] Filed: Sep. 29, 1978

[51] Int. Cl.$^2$ .............................................. A61C 3/00
[52] U.S. Cl. ...................................................... 433/5
[58] Field of Search ............................ 32/14 D; 433/5

[56] References Cited

U.S. PATENT DOCUMENTS

| | | | |
|---|---|---|---|
| 3,866,322 | 2/1975 | Broussard et al. | 32/14 D |
| 4,121,341 | 10/1978 | DeWoskin | 32/14 D |

*Primary Examiner*—Robert Peshock
*Attorney, Agent, or Firm*—Fishauf, Holtz, Goodman & Woodward

[57] ABSTRACT

An orthodontic face bow for applying at least extrusion and/or intrusion forces to teeth in a controlled and reliable manner comprises an inner bow member having first and second ends to be coupled to respective teeth in the mouth; and an outer bow member coupled to the inner bow member at a substantially central portion thereof, the inner and outer bow members being rotatable relative to each other. A resilient biasing means is coupled between the inner and outer bow members for resiliently biasing one of the bow members relative to the other to cause one of the bow members to rotate relative to the other to apply at least one of the aforementioned extrusion and intrusion forces to the teeth to which the inner bow member is coupled. Also disclosed is an arrangement in which the inner and outer bow members are both mounted intra-oral and further arrangements which limit the amount of rotation of one of the bow members relative to the other.

36 Claims, 23 Drawing Figures

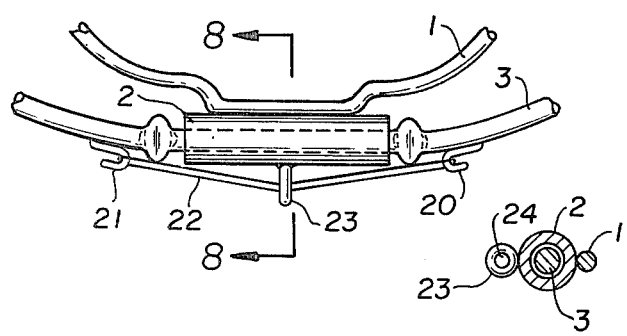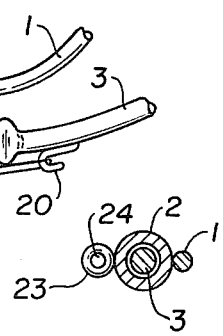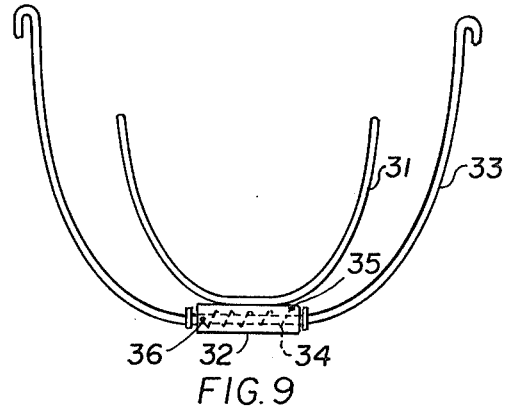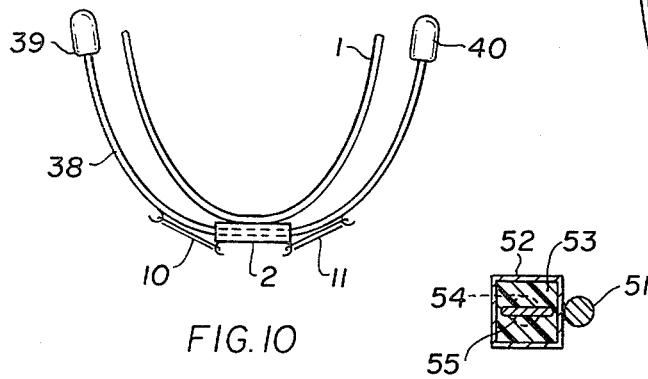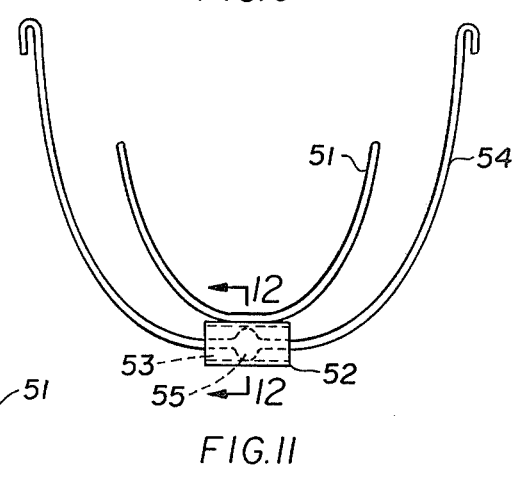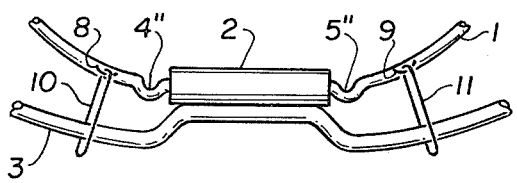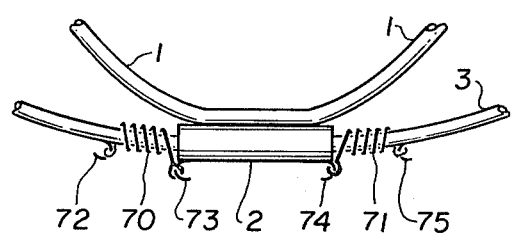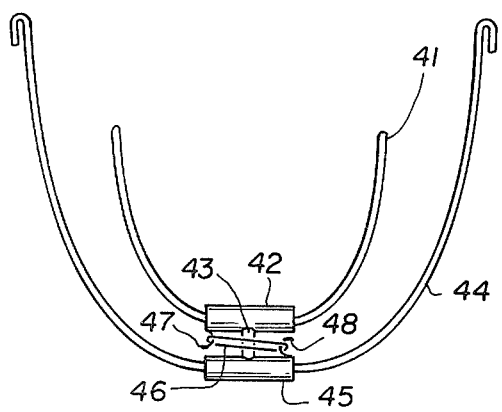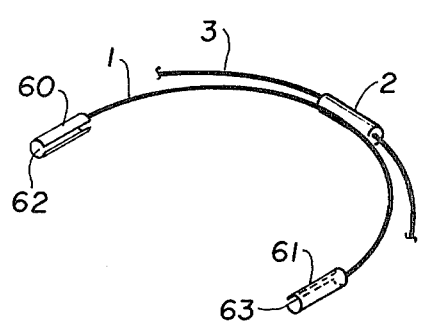

ORTHODONTIC FACE BOW

BACKGROUND OF THE INVENTION

This invention relates to orthodontic headgear, generally termed "nightbrace" or "face bow", and more particularly to an improved orthodontic headgear which provides intrusion or extrusion forces as well as the conventional rearwardly directed forces.

Conventional face bows comprise an inner bow member, made of wire, which engages buccal tubes which are fixed on respective teeth on opposite sides of the mouth. An outer bow, of wire, is connected to the inner bow at a forward end thereof and extends around the outside of the patient's face and engages an elastic or other biassing arrangement which extends around the back of the head of the patient. Typical face bows are illustrated, for example, in U.S. Pat. Nos. 4,087,915; 3,337,958; and 3,303,566.

The object of the present invention is to provide an orthodontic headgear or face bow which, in addition to the conventional rearwardly directed forces, provides intrusion or extrusion forces to the teeth to which the inner bow is attached in a simple and controllable manner.

It is a further object of the invention to provide such a face bow with inner and outer bows which are movably connected relative to each other and which has conveniently arranged biassing means coupled to the inner and outer bows.

SUMMARY OF THE INVENTION

In accordance with the present invention, an orthodontic face bow for applying at least extrusion and/or intrusion forces to teeth comprises: an inner bow member having first and second ends to be coupled to respective teeth in a mouth; and an outer bow member coupled to the inner bow member at a substantially central portion thereof, the inner and outer bow members being rotatable relative to each other. Further provided is resilient biassing means coupled between the inner and outer bow members for resiliently biassing one of the bow members relative to the other of the bow members to cause one of the bow members to rotate relative to the other to apply at least one of the aforementioned extrusion and intrusion forces to the teeth to which the inner bow is coupled.

BRIEF DESCRIPTION OF THE DRAWINGS

FIG. 7 is a partial top view of still another embodiment of the invention;

FIG. 8 is a sectional view taken along the line 8—8 in FIG. 7;

FIG. 9 is a top view of yet another embodiment of the invention;

FIG. 10 is a top view of another embodiment of the invention;

FIGS. 11 and 12 are top and sectional views, respectively, of still another embodiment of the invention;

FIG. 13 is a partial top view of yet another embodiment of the invention;

FIG. 14 is a partial top view of still another embodiment of the invention;

FIG. 15 is a top view of another embodiment of the invention providing rotational relationships in a different plane from the previously described embodiments;

FIG. 16 is a partial perspective view illustrating connection means for connecting the inner bow to, for example, an arch wire;

DETAILED DESCRIPTION

Figure 1:
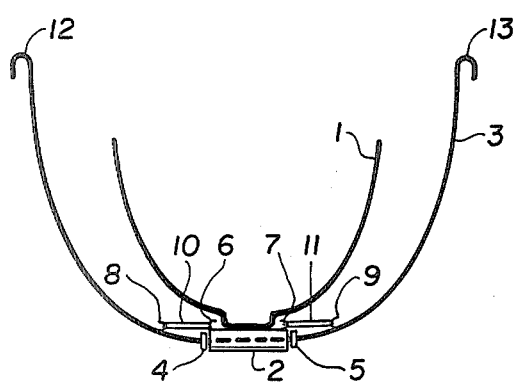
FIG. 1 is a top view of a face bow according to the present invention.
Figure 2A:
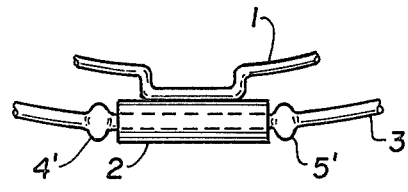
FIGS. 2a and 2b are partial views of modifications of the face bow of FIG. 1.
Figure 2B:
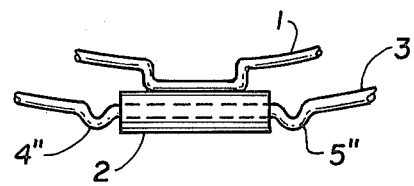

Referring to FIG. 1, the orthodontic appliance of the present invention comprises an inner bow 1 which is fixedly connected to a tubular member 2, for example by soldering. The outer bow 3 passes through the tubular member 2 and is rotatable in the tubular member about the longitudinal axis thereof. Stop members 4, 5 such as washers, disks, or the like, are secured to outer bow 3, for example by soldering, to retain the outer bow within the tubular member 2. In place of stop members 4, 5, portions of the outer bow could be deformed, such as shown in FIGS. 2a and 2b. In FIG. 2a, the deformed areas 4', 5' are formed by, for example, impacting the wire outer bow 3 to form the flattened and spread portions 4', 5'. In FIG. 2b, the deformed areas 4", 5" comprise bent portions of the wire. The stop members 4, 5; 4', 5'; 4", 5"; or any suitable variation, may be used interchangeably in the illustrated embodiments. The stop members may also take the form of integral loops in the wire.

Hooks 6, 7 are provided on tubular member 2, preferably at opposite ends thereof, and hooks 8, 9 are provided on outer bow 3, at portions thereof on opposite sides of the tubular member 2. Extending between hooks 6 and 8 is a first rubber band, or the like 10 and extending between hooks 7 and 9 is a second rubber band, or the like 11. The outer face bow has hooks 12, 13 for engaging a headgear, such as an elastic headband (not shown) with which the outer bow cooperates to impart rearwardly directed forces to the teeth to which the inner bow 1 are connected. The headband need not be elastic when it is not desired to impart rearwardly directed forces to the teeth.

While the hooks 6 and 7 are shown on opposite ends of the tube 2, is should be clear that they may be placed anywhere along tube 2, as is convenient. Also, the hooks 8, 9 on outer bow 3 may be placed at other positions along the length of the outer bow, the hooks 8, 9 preferably being located on opposite sides of the tubular member 2 so that the biassing forces imparted by the rubber bands 10, 11 are balanced. The term "rubber bands" is used generically herein to denote elastic members which have loop-type or other connectors for engaging the respective hooks 6–9. The elastic members may be fabricated of rubber or any other elastomeric material, as desired.

Figure 3:
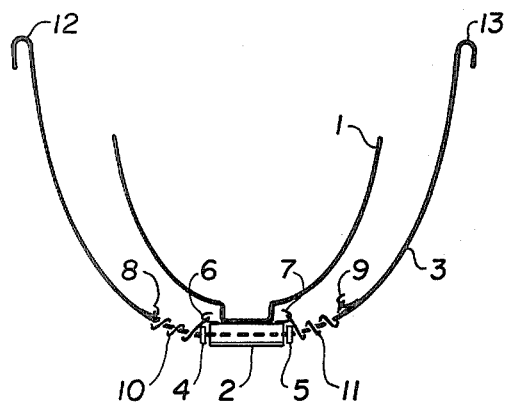
FIG. 3 illustrates the face bow of FIG. 1.

In operation, the outer bow is wound relative to the inner bow so as to cause the rubber or elastic bands 10, 11 to become tensioned and wound around the outer bow 3, for example as illustrated in FIG. 3. The tensioning of the elastic bands 10, 11 causes the outer bow 3 to tend to unwind relative to the inner bow 1. When in the wound state as illustrated in FIG. 3, the bow 1 is inserted into the mouth to be engaged with, for example, buccal end tubes on respective teeth in the mouth, as is conventional. The headband is engaged with hooks 12, 13 of outer bow 3 while the outer bow is in the wound or tensioned state. In this condition, the inner bow 1 will be biassed so as to rotate relative to the outer bow 3, thereby producing intrusion or extrusion forces on the teeth to which it is attached, depending upon which way the bows 1 and 3 were wound relative to each other. The bows may be wound in either direction relative to each other. If it is desired to have the bows wind in only a single direction, the direction of force applied to the teeth can be reversed merely by turning the device upside down before engaging it with the teeth.

Figure 4:
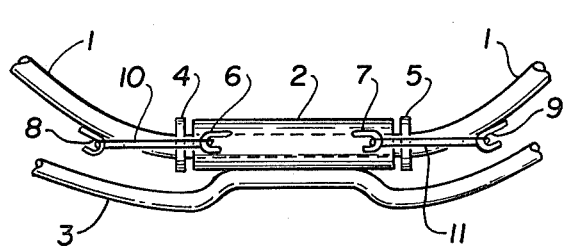
FIG. 4 is a partial top view of another embodiment of the invention.

As shown in FIG. 4, in an alternative arrangement, the inner bow 1 may be rotatably mounted in the tubular member 2 and the outer bow 3 may be fixedly secured to the tubular member 2. Since the inner bowl can be wound less than one-half turn relative to the outer bow 3 in the FIG. 4 embodiment, strong elastomeric bands or the like 10, 11 must be used, with the hooks 6–9 suitably arranged so that a small relative turning of the bows provides sufficient biassing forces.

Figure 5:
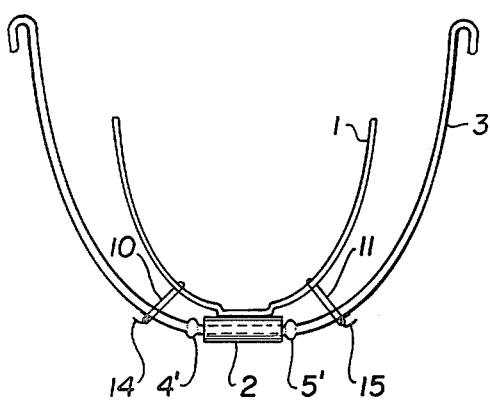
FIG. 5 is a top view of another emobodiment of the invention.

FIG. 5 illustrates a modification of the embodiment of FIG. 3 wherein the elastic bands 10, 11 are merely slipped over the inner bow 1 and are engaged with respective hooks 14, 15 provided on the outer bow 3. The operation of this embodiment is substantially similar to that of FIG. 3. The bows may be wound in either direction relative to each other so as to wind the elastic bands 10, 11 around the outer bow 3 to produce the biassing force.

The particular connection of the elastic bands 10, 11 to the inner bow 1, outer bow 3 and tubular member 2 may be varied, as desired, the critical feature being that the inner bow is rotatable or movable relative to the outer bow and is biassed relative to the outer bow by means of one or more elastic bands 10, 11. The elastic bands 10, 11 are readily replaceable, even by the patient, should one or more of them break during use.

Figure 6A:
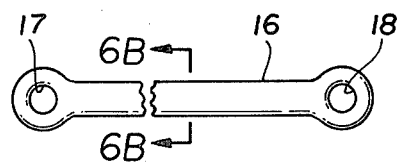
FIGS. 6A and 6B show top and sectional views, respectively, of an elastic band useful in the present invention.
Figure 6B:

Special elastic bands, such as band 16 illustrated in FIGS. 6A and 6B can be used. The band 16 has apertures 17, 18 at opposite ends thereof for engagement with, for example, hooks on the various bows or tubular member or for engagement over one of the bow members, for example as illustrated in FIG. 5.

FIGS. 7 and 8 illustrate another embodiment of the invention wherein the tubular member 2 has a loop member 23 attached thereto, the loop member having an aperture 24 (FIG. 8) therein through which an elastic band 22, or the like is passed. The elastic band engages at opposite ends thereof with respective hooks 20, 21 on outer bow 3. The embodiment of FIGS. 7 and 8 operates substantially similarly to the embodiment of FIGS. 1 and 3. The ring member 23 may be an elongated tubular member or a hook member to engage an intermediate portion of the elastic band 22.

The embodiment of FIG. 7 could be modified, as should be apparent, by fixing the outer bow 3 to the tubular member and by mounting the inner bow 1 so that it is rotatable within the tubular member 2, for example similar to the embodiment of FIG. 4. As mentioned with respect to FIG. 4, relative rotation is very limited in such a modified arrangement.

FIG. 9 illustrates a further embodiment of the invention wherein the inner bow 31 is fixedly connected to a tubular member 32 and an outer bow 33 is rotatably mounted within the tubular member 32, as in the FIGS. 1, 5, 7 and 8 embodiments. The biassing arrangement in this embodiment is recessed within the tubular member 32, and comprises a coil-type spring 34 which is anchored at one end 35 to the tubular member 2 and which is anchored at the other end 36 to the outer bow 33. In use, the outer bow is wound relative to the inner bow in order to tighten or wind up the spring 34. After winding of the bows relative to each other, the apparatus is installed in the mouth, as in the other embodiments. To change the direction of force on the teeth, it is only necessary to turn the device upside down so that the force is directed in the opposite direction or to wind the bows in the opposite direction to unwind the coil toward an overopen state.

FIG. 10 illustrates an embodiment of the invention wherein the outer bow has ends which are adapted to be located within the mouth, rather than extending around the outside of the face of the wearer. The inner bow 1 is fixedly connected to the tubular member 2, for example as shown in FIG. 1. The outer bow member 38 rotatably passes through tubular member 2 and hooks are provided between which are mounted elastic bands 10, 11. At the ends of bow member 38 are cushioned members 38, 40 which are adapted to be inserted within the mouth and engage against either the upper or lower area of the mouth cavity between the teeth and the cheeks. The bows 1, 38 are, of course, wound relative to each other to wind the elastic bands 10, 11 as shown in FIG. 3 prior to insertion in the mouth. This arrangement obviates the necessity for a strap, or the like, extending around the outside of the face of the wearer. The size, shape and location of the end members 39, 40 may be varied, depending upon the portions of the inner mouth cavity against which it is desired that the ends bear. The end members 39, 40 are preferably made of resilient material, such as elastomeric material, so as to be more comfortable to the patient.

FIGS. 11 and 12 illustrate a still further modified embodiment of the invention wherein a block or mass of elastomeric material, such as rubber, is used as the biassing means in place of the elastic bands and springs discussed hereinabove. In FIG. 11, the inner bow 51 is fixedly connected to an elongated tubular member 52. A mass of elastomeric material 53 is within elongated member 52 and the outer bow 54 passes therethrough. The outer bow 54 has a flattened portion 55, bent portion (similar to bent portion in FIG. 2b), or the like, which prevents the outer bow 54 from rotating or moving axially relative to the elastomeric block 53. In use, the arrangement of FIGS. 11 and 12 may be fabricated so that the inner bow 51 is offset relative to the outer bow 54 by a predetermined number of degrees, or the elastomeric material is made resilient enough so that the bows can be "wound" like a spring relative to each other as in the previously described enbodiments. When the device is inserted in the mouth and the outer bow is secured to a headgear, or mounted in the mouth as in FIG. 10, the two bows 51 and 54 apply a biassing force to the teeth (intrusion or extrusion) due to the biassing forces exerted by the block or strip of elastomeric material 53. This creates the desired orthodontic force. This arrangement is particularly useful in an embodiment of FIG. 10 wherein the ends of the outer bow are adapted to be inserted in the mouth and to bear against inner portions of the upper or lower mouth cavities outside of the teeth.

FIG. 13 illustrates an embodiment of the invention wherein the outer bow 3 is fixedly connected to the tubular member 2 and the inner bow 1 is rotatably mounted within the tubular member 2. The inner bow 1 has bent portions 4", 5" to retain same within the tubular member 2. Hooks 8, 9 extend from inner bow 1 for engaging elastic bands 10, 11, respectively, which are passed over the outer bow member 3. The bands 10, 11 are shown loosely engaged in FIG. 13 for ease of illustration, but they are generally maintained rather tight so as to bias the inner bow member to extend in a direction out of the paper toward the viewer as seen in FIG. 13. This arrangement provides about one quarter turn of the inner bow relative to the outer bow against the biassing force of elastic bands 10, 11. The hooks 8, 9 may project upwardly as seen in FIG. 13, or may project downwardly in the opposite direction, as desired. The direction of the hooks 8, 9 will determine the direction of application of biassing force.

FIG. 14 illustrates an embodiment using coil springs, similar to FIG. 9, but with two coil springs 70, 71 around outer bow member 3, the coil springs being respectively engaged, for example by loops at the ends thereof, to respective hooks 72-75 on outer bow 3 and tubular member 2. This embodiment is operated in the same manner as the previous embodiments wherein the outer bow member is rotatably mounted in the tubular member 2.

FIG. 15 illustrates a further modification of the invention in which the inner and outer bows are rotatably mounted relative to each other such that one of the bows rotates about an axis which is perpendicular to the bows at the point of rotation. The inner bow 41 is mounted, preferably fixedly, to an intermediate member 42 having a shaft 43 extending therefrom. The outer bow 44 is mounted, preferably fixedly, to an intermediate member 45 which is connected to the shaft 43. One or both of the members 42, 45 are pivotally mounted to the shaft 43 so that the members 42, 45 are rotatable relative to each other about the longitudinal axis of shaft 43. An elastic band 46 is mounted between hooks 47, 48 projecting from members 42 and 45, respectively. In operation, the outer and inner bows are rotated relative to each other about the longitudinal axis of shaft 43 so as to wind the elastic band 46 about the shaft. This creates a tension force on the band 46 which tends to cause the bows to unwind relative to each other. In the wound state, the inner bow is mounted to the teeth and the outer bow is secured to a headgear. Since the bows will tend to rotate relative to each other about the axis of shaft 43, the orthodontic arrangement of FIG. 15 will provide oppositely directed forces at the respective ends of the inner bow 41 (i.e., extrusion forces at one end of inner bow 41 and extrusion forces at the outer end of inner bow 41).

One or more elastic bands may be used in the embodiment of FIG. 15. Moreover, the intermediate members 42, 45 may be pivotally connected to each other without using a shaft 43 in between, for example by means of a rivet connecting the two members.

Throughout the application, the inner bow member has been described as being engageable with buccal tubes mounted to teeth. However, it should be clear that appropriate connection means can be provided at the ends of the inner bows to engage hooks, arch wires or other auxiliaries in the mouth. A typical example of an inner bow with arch wire engaging hooks 60, 61 is shown in FIG. 16. Cylindrical hooks 60, 61 have axial slots 62, 63, respectively which snap over an arch wire to engage the arch wire. The hooks 60, 61 in FIG. 16 may be varied as desired.

Figure 17:
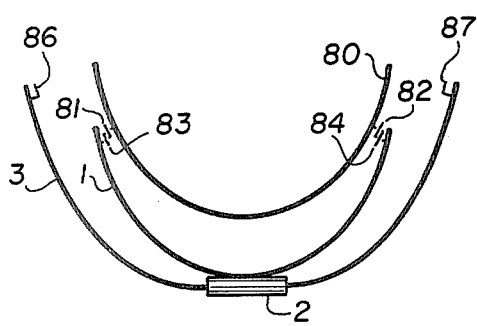
FIG. 17 is a partial top view illustrating connection means for connecting the inner bow to, for example, hooks mounted in the mouth.

FIG. 17 illustrates an inner bow member 1 having appropriate attachments or hooks 81, 82 thereon to engage other attachments or hooks 83, 84 which are on, for example, an arch wire 80. The inner and outer bows 1, 3 are rotated relative to each other and are appropriately biassed by means such as described hereinabove, and the inner member 1 is placed in the mouth with the hooks or attachments 81, 82 in engagement with arch wire hooks or attachments 83, 84, respectively. The outer bow member is either fixed to a headgear or is mounted also within the mouth such as shown in connection with FIG. 10. The hooks or attachments 83, 84 need not be mounted to arch wires—they may be mounted to brackets, bands, bite plates, overlays, removable appliances or otherwise secured to appropriate teeth to which orthodontic forces are to be applied.

Figure 18:
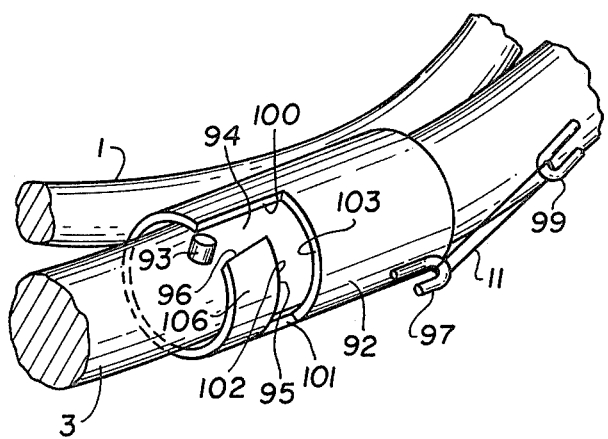
FIG. 18 is a partial perspective view of a mechanism for preventing the outer bow from uncontrollably unwinding relative to the inner bow after the elastic bands, springs, or the like, are tensioned or biassed.

FIG. 18 illustrates an embodiment wherein uncontrolled rotation or spinning of the outer bow member relative to the inner bow member, after tensioning of the biassing bands or spring, is prevented. FIG. 18 illustrates only the rotation preventing means, this means being usable on any of the embodiments of the invention described hereinabove. For illustration purposes, one elastic band 11 connected between respective hooks 97, 99 is illustrated in FIG. 18. Inner bow 3 has an extending or protruding member 93 thereon. After the outer bow 3 is wound relative to the inner bow 1 to wind up the elastic band 11 (and its counterpart on the other side of tube 92), the inner bow 3 is shifted to the right so that the protrusion 93 may pass through an axial slot or cut-out 94 in tubular member 92. The protruding member 93 is then engaged in circumferential slot 95 of tubular member 92. In the position where the protrusion 93 is engaged in circumferential slot 95, the outer bow 3 is prevented from unwinding in either direction (depending upon the direction in which the band 11 was wound) by abutment of the protruding member 93 with surfaces 100, 101 of circumferential slot 95. The locations of abutment surfaces 100, 101 of tubular member 92 may be varied, depending upon the degree of rotation of outer bow 3 which is to be permitted. This construction prevents inadvertent or undesired controlled unwinding of outer bow member 3 so as to make use of the device by the patient safer.

Since the circumferential slot 95 is interior of the ends of the tubular member 92, the slot 95 will retain the outer bow 3 in its desired position within the tubular member 92 by abutment of the projection 93 against surfaces 102, 103 of circumferential slot 95. This renders it unnecessary to provide retainer members 4, 5; 4', 4';

4", 5". Cut-out or slot 94 has an inclined surface 96 to progressively narrow slot 94. The protrusion 93 is forced past the narrow part of slot 94 to "snap" into circumferential slot 95. This prevents protrusion 93 from inadvertently coming out of slot 95. Protrusion 93 can be removed from slot 95 by the doctor by, for example, lifting cylinder portion 106 over protrusion 93.

Figure 19:
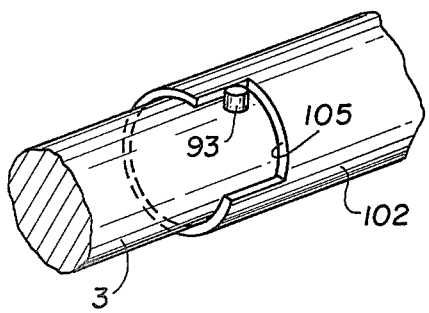
FIG. 19 is a partial perspective view of a modified mechanism for preventing the outer bow from uncontrollably unwinding relative to the inner bow.

A simplified modification of the arrangement of FIG. 18 is shown in FIG. 19 wherein the projection 93 is located within a cut-out 105 of tubular member 102. In this embodiment, retaining means such as means 4, 5, or the like, is preferably provided to prevent axial movement of outer bow 3 relative to tubular member 102. Again, FIG. 19 illustrates only a small portion of the overall device for ease of illustration of the principle of preventing uncontrolled rotation of the wound or tensioned outer bow 3.

Figure 20:
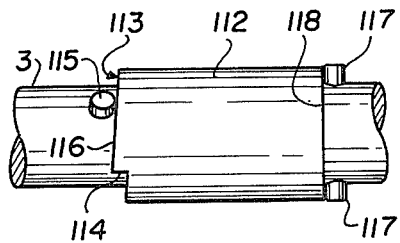
FIG. 20 is a partial perspective of yet another embodiment of a mechanism for preventing the outer bow from uncontrollably unwinding relative to the inner bow.

FIG. 20 illustrates another embodiment for preventing uncontrolled reverse rotation of outer bow 3. In FIG. 20, the tubular member 112 has a ratchet-type cammed surface 113 at one or both ends thereof, the cam surface 113 having a step 114 formed therein. Outer bow 3 has a projection 115 extending therefrom which is resilient enough to yield as it "rides" along inclined surface 116 of cam surface 113 during winding or tensioning of the outer bow 3 and snaps back after passing stepped portion 114. The other end of outer bow 3 may have similar resilient members 117 which merely bear against end surface 118 of tubular member 112 to prevent axial movement of outer bow 3 relative to tubular member 112. Members 117 may have a dished washer between them and surface 118 to provide a spring loaded stop which permits limited spring loaded axial movement as projection 115 rides on cam surface 113. In this embodiment, using only one step 114, the maximum reverse uncontrolled rotation of outer bow 3 is one turn. If more steps 114 are provided, the maximum uncontrolled degree of rotation can be reduced. While FIG. 20 illustrates a cammed surface on only one end of tubular member 112, a similar cammed surface may be provided in place of substantially straight surface 118 at the other end thereof. Thus, the tubular member 112 may comprise cammed surfaces at one or both ends thereof.

Figure 21:
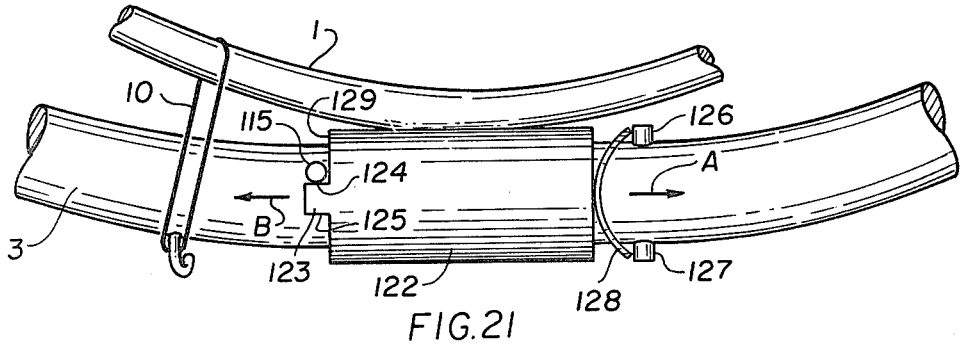
FIG. 21 is a partial side view of a modification of FIG. 20.

FIG. 21 illustrates a modification of the embodiment of FIG. 20. In FIG. 21, the tubular member 122 has a projecting portion 123 with abutment surfaces 124, 125. The outer bow member 3, which is rotatably mounted within tubular member 122, has a projection 115 thereon which selectively engages abutment surfaces 124, 125. The outer bow member 3 has further projections or deformations 126, 127 on the other side of tubular member 122, with a dished washer 128 located between projections 126, 127 and the end of tubular member 122. The dished washer 128 is preferably made of spring-type material so as to spring load the outer bow member 3 in the direction of arrow A in FIG. 21. Dished washer 128 may be replaced by, for example, a coil spring, in an elastomeric washer, or other suitable biassing device. One elastomeric band 10 is shown connected between a hook on outer bow member 3 and inner bow member 1. A similar elastic band is preferably provided on the other side of tubular member 122, but is not shown for ease of illustration. In use, the operator pulls the outer bow member in the direction of arrow B in FIG. 21 and winds up the elastomeric bands, or other biassing devices, in the desired direction. After winding the desired number of turns, the operator releases the pull on outer bow member 3 and the dished washer 128 causes the bow member 3 to move in the direction of arrow A so that projection 115 bears upon end surface 129 of tubular member 122. The projecting portion 123 serves to prevent uncontrolled unwinding of the outer tubular member since the projection 115 will bear against one of abutment surfaces 124, 125, depending upon which direction the outer bow member 3 was wound relative to the inner bow member 1. If desired, additional projections 123 may be provided spaced around the tubular member 122 to limit the rotation of the bow members to smaller increments.

In the embodiment of FIG. 17, the outer bow member 3 may be provided with hooks 86, 87 at the ends thereof, or intermediate the ends thereof for engagement with an orthodontic appliance in the mouth of the wearer. The hooks 86, 87 may be adapted to be engaged with orthodontic appliances on the same arch as hooks 81, 82, or may be engaged with orthodontic appliances on the opposite arch.

While the embodiment of FIG. 10 is shown as being a completely intra-oral engagement device, it should be clear that any of the other embodiments of the invention may be modified by suitably arranging the outer bow member so as to be substantially similar at its ends and curvature to that of FIG. 10 for engaging either intra-oral mouth portions of the wearer, or for engaging intra-oral orthodontic appliances mounted to the teeth of the patient.

I claim:

1. An orthodontic face bow for applying at least extrusion and/or intrusion forces to teeth, comprising:
   an inner bow member having first and second ends to be coupled to respective teeth in a mouth;
   an outer bow member coupled to said inner bow member at a substantially central portion thereof;
   said inner and outer bow members being rotatably relative to each other;
   resilient biassing means coupled between said inner and outer bow members for resiliently biassing one of said bow members relative to the other of said bow members to cause one of said bow members to rotate relative to the other to apply at least one of said extrusion and intrusion forces to the teeth to which said inner bow is coupled; and
   means coupled to at least one of said inner and outer bow members for limiting the rotational movement of said inner and outer bow members relative to each other against the relative rotational forces applied by said resilient biassing means to prevent inadvertent unwinding of one bow member relative to the other, thereby preventing injury to a wearer.

2. The face bow of claim 1 wherein said inner and outer bow members are spaced from each other and said resilient biasing means comprises a mass of elastomeric material fixedly and nonrotationally coupled between said inner and outer bow members in said space, said mass of elastomeric material substantially filling said space at least along a substantial longitudinal portion of said inner and outer bow members, the resilient biasing being provided by internal yielding of said mass of resilient material due to rotational displacement of said inner and outer bow members relative to each other.

3. The face bow of claim 1 comprising a generally tubular member coupled to one of said inner and outer bow, the other of said inner and outer bows being rotatably mounted within said tubular member so as to rotate about the longitudinal axis of said tubular member, said other of said bows being spaced from said tubular member, said elastomeric material substantially filling said space between said tubular member and said other bow.

4. The face bow of claim 1, comprising stop means coupled to one of said inner and outer bow members, and further comprising abutment means coupled to the other of said inner and outer bow members for abutting against said stop means to limit relative rotation therebetween.

5. The face bow of claim 1 comprising a tubular member coupled to one of said inner and outer bow members, the other of said bow members being rotatably mounted within said tubular member and being rotatable about the longitudinal axis of said tubular member, said tubular member having a cutout portion defining at least one stop means, said bow member which is mounted within said tubular member comprising abutment means adapted to abut against said stop means to limit rotation of said bow member mounted within said tubular member relative to said tubular member.

6. The face bow of claim 5, wherein said cut-out has a reentrant portion for receiving said abutment member, said reentrant portion comprising means for substantially preventing axial movement of said bow member mounted within said tubular member relative to said tubular member.

7. The face bow of claim 1, wherein said means for limiting relative rotation comprises camming means coupled to at least one of said inner and outer bow members and engagement means coupled to the other of said inner and outer bow members for engaging said camming means.

8. The face bow of claim 7, wherein said camming means comprises a ratchet-type stepped surface which permits unidirectional movement of said engagement means on said camming surface.

9. The face bow of claim 1, wherein the said means for limiting relative rotation comprises a projection coupled to one of said inner and outer face bows and defining abutment surfaces on opposing sides of said projection, and engagement means coupled to the other of said inner and outer bow members for selectively engaging one of said abutment surfaces, depending upon the direction of biassing of said resilient biassing means.

10. The face bow of claim 9, comprising a tubular member coupled to said one of said inner and outer face bows, said tubular member comprising said projecting means extending from an end thereof; and wherein said other bow member comprises means for resiliently retaining said other bow member in a given axial position of said other bow member, said other bow member being axially displaceable with said tubular member against said resilient retaining means to disengage said engagement means for said abutment means.

11. An orthodontic face bow for applying at least extrusion and/or intrusion forces to teeth, comprising:
an inner bow member having first and second ends to be coupled to respective teeth in a mouth;
an outer bow member;
coupling means (FIG. 4) rotatably coupling said inner bow member to said outer bow member at a substantially central portion thereof so that said inner and outer bow members are rotatably relative to each other about an axis substantially perpendicular to the axial direction of the bow members where they are coupled together; and
resilient biassing means coupled between said inner and outer bow members for resiliently biassing one of said bow members relative to the other of said members to cause one of said bow members to rotate relative to the other about said axis to apply extrusion to a tooth coupled to one end of said inner bow and intrusion forces to a tooth coupled to the other end of said inner bow.

12. The face bow of claim 11, wherein said coupling means is coupled between said inner and outer bow members at substantially central portions thereof for permitting said rotational movement.

13. The face bow of claim 12, wherein said rotatable coupling means comprises a member interposed between said inner and outer bows at substantially the central portions thereof, said member being rotatably coupled to at least one of said inner and outer bows for rotation of said inner and outer bows about said axis substantially perpendicular to the axes of said inner and outer bows at the area of connection therebetween.

14. The face bow of claim 12, wherein said resilient biassing means comprises an elastic band coupled between said inner and outer bow members.

15. An orthodontic face bow for applying at least extrusion and/or intrusion forces to teeth, comprising:
an inner bow member having first and second ends to be coupled to respective teeth in a mouth;
an outer bow member;
a generally tubular member coupled to one of said inner and outer bow members at a substantially central portion of said at least one bow member, the other of said bow members being rotatably mounted within said tubular member with a space therebetween so as to rotate about the longitudinal axis of said tubular member, said inner and outer bow members being rotatably relative to each other; and
resilient biasing means coupled between said inner and outer bow members for resiliently biasing one of said bow members relative to the other of said bow members to cause one of said bow members to rotate relative to the other to apply at least one of said extrusion and intrusion forces to the teeth to which said inner bow is coupled;
said resilient biasing means comprising a mass of elastomeric material fixedly and non-rotationally coupled between said tubular member and said other of said bow members in said space, said mass of elastomeric material substantially filling said space at least along a substantial longitudinal portion of said tubular member, the resilient biasing being provided by internal yielding of said mass of resilient material due to rotational displacement of said inner and outer bow members relative to each other.

16. The face bow of claim 15, wherein said mass of elastomeric material is an elongated cylindrical mass extending along a major portion of the length of said tubular member.

17. The face bow of any one of claims 1, 11 or 16, wherein said outer bow member includes means at the ends thereof for abutting against an intra-oral mouth portion of a wearer.

18. The face bow of claim 17, wherein said intra-oral abutment means comprises resilient means at the end portions of said outer low member.

19. An intra-orally engaging orthodontic face bow for applying at least extrusion and/or intrusion forces to teeth, comprising:
- an inner bow member having first and second ends to be intra-orally coupled to respective teeth in a mouth;
- an outer bow member coupled to said inner bow member at a substantially central portion thereof, said outer bow member having respective ends which include means for intra-oral engagement in the mouth of a wearer;
- said inner and outer bow members being rotatably relative to each other; and
- resilient biasing means coupled between said inner and outer bow members for resiliently biasing one of said bow members relative to the other of said bow members to cause one of said bow members to rotate relative to the other to apply at least one of said extrusion and intrusion forces to the teeth to which said inner bow is coupled.

20. The face bow of claim 19 wherein said intra-oral engagement means at the ends of said bow member each comprise means for abutting against an intra-oral mouth portion of a wearer.

21. The face bow of claim 20, wherein said intra-oral abutment means comprises resilient means at the end portions of said outer bow member.

22. The face bow of claim 19 wherein said intra-oral engagement means at the ends of said outer bow member each comprise means for engaging an intra-oral orthodontic appliance.

23. The face bow of any one of claims 1, 11, 16 or 19 wherein said inner bow member comprises means at an least one end thereof for engaging an arch wire, or the like.

24. The face bow of claim 23, wherein said arch wire engaging means comprises a substantially cylindrical member having an axial cut-out portion therein through which said arch wire is engaged into the inner area of said cylindrical member.

25. The face bow of claim 23, wherein said inner bow member comprises an arch wire engaging means at each end thereof.

26. The face bow of claim 23, wherein said arch wire engaging means comprises hook means.

27. The face bow of claim 23 wherein said outer bow member comprises engagement means at ends thereof for engaging an intra-oral orthodontic appliance.

28. The face bow of claim 23, wherein said engagement means of said outer bow member comprises hook means.

29. An orthodontic face bow for applying at least extrusion and/or intrusion forces to teeth, comprising:
- an inner bow member having first and second ends to be intra-orally coupled in a mouth of a wearer, at least one of said ends including means for engaging an arch wire, or the lie, in the wearer's mouth;
- an outer bow member coupled to said inner bow member at a substantially central portion thereof;
- said inner and outer bow members being rotatably relative to each other; and
- resilient biasing means coupled between said inner and outer bow members for resiliently biasing one of said bow members relative to the other of said bow members to cause one of said bow members to rotate relative to the other to apply at least one of said extrusion and intrusion forces to the teeth to which said inner bow is coupled.

30. The face bow of claim 29, wherein said arch wire engaging means comprises a substantially cylindrical member having an axial cut-out portion therein through which said arch wire is engaged into the inner area of said cylindrical member.

31. The face bow of claim 29, wherein said inner bow member comprises an arch wire engaging means at each end thereof.

32. The face bow of claim 29, wherein said arch wire engaging means comprises hook means.

33. The face bow of claim 29, wherein said outer bow member comprises engagement means at the ends thereof for engaging an intra-oral orthodontic appliance.

34. The face bow of claim 33, wherein said engagement means of said outer bow member comprises hook means.

35. An orthodontic face bow for applying at least extrusion and/or intrusion forces to teeth, comprising:
- an inner bow member having first and second ends to be coupled to respective teeth in a mouth;
- an outer bow member coupled to said inner bow member at a substantially central portion thereof;
- said inner and outer bow members being rotatable relative to each other; and
- resilient biasing means coupled between said inner and outer bow members for resiliently biassing one of said bow members relative to the other of said bow members to cause one of said bow members to rotate relative to the other to apply at least one of said extrusion and intrusion forces to the teeth to which said inner bow is coupled;
- said resilient biassing means comprising at least one elongated rubber-band-type elastic member coupled between said inner and outer bow members and adapted to be wound around at least one of said bow members to develop a resilient biassing force to cause one of said bow members to rotate relative to the other.

36. The face bow of claim 35 wherein each of said bow members comprises a hook and said resilient rubber-band-type elastic member comprises loop means at each end thereof for engaging a respective hook means.

* * * * *

UNITED STATES PATENT AND TRADEMARK OFFICE
CERTIFICATE OF CORRECTION

PATENT NO. : 4,224,022

DATED : September 23, 1980

INVENTOR(S) : Melvin Wallshein

It is certified that error appears in the above-identified patent and that said Letters Patent are hereby corrected as shown below:

Column 2, line 66, after "2," change "is" to --it--;

Column 9, line 62, after "coupling means" change "(FIG. 4)" to --(FIG. 15)--;

Column 11, line 34 (claim 23), change "at an" to --at at--;

Column 11, line 49 (claim 27), change "ends" to --the ends--.

Column 3, line 34, change "inner bowl" to --inner bow--;

Column 10, last line, change "low" to --bow--;

Column 12, line 2, change "or the lie" to --or the like--.

Signed and Sealed this

Thirteenth Day of January 1981

[SEAL]

Attest:

SIDNEY A. DIAMOND

Attesting Officer

Commissioner of Patents and Trademarks